United States Patent
Bunch et al.

[11] Patent Number: 5,576,281
[45] Date of Patent: Nov. 19, 1996

[54] BIOGRADABLE LOW FOAMING SURFACTANTS AS A RINSE AID FOR AUTODISH APPLICATIONS

[75] Inventors: Henry S. Bunch, Stamford; Theodore Groom, Northford; Frank R. Grosser, Bethany; Michael Scardera, Hamden; Tom S. Targos, New Haven, all of Conn.; Arthur R. Vanover, Brandenburg, Ky.

[73] Assignee: Olin Corporation, Cheshire, Conn.

[21] Appl. No.: 43,108

[22] Filed: Apr. 5, 1993

[51] Int. Cl.⁶ .................................. C11D 1/68
[52] U.S. Cl. .............. 510/220; 252/358; 568/606; 568/618; 568/622; 568/625; 510/221; 510/506; 510/514; 510/413; 510/421
[58] Field of Search .......... 252/174.22, 174.21, 252/174.19, 95, 135, 358, DIG. 1; 568/625, 622, 618, 606

[56] References Cited

U.S. PATENT DOCUMENTS

| | | | |
|---|---|---|---|
| 3,956,401 | 5/1976 | Scardera et al. | 260/615 B |
| 4,207,421 | 6/1980 | Scardera et al. | 568/625 |
| 4,317,940 | 3/1982 | Scardera et al. | 568/625 |
| 4,762,637 | 8/1988 | Aronson et al. | 252/99 |
| 4,827,028 | 5/1989 | Scardera et al. | 562/583 |
| 4,863,632 | 9/1989 | Aronson et al. | 252/186.35 |
| 4,898,621 | 2/1990 | Pruehs et al. | 134/25.2 |
| 4,925,587 | 5/1990 | Schenker et al. | 252/174.22 |
| 4,994,626 | 2/1991 | Greenough et al. | 568/618 |
| 5,281,351 | 1/1994 | Romeo et al. | 252/99 |
| 5,294,365 | 3/1994 | Welch et al. | 252/174.22 |

*Primary Examiner*—Ponnathapura Achutamurthy
*Attorney, Agent, or Firm*—Dale L. Carlson

[57] ABSTRACT

The present invention relates to a poly(oxyalkylated) alcohol composition represented by the formula:

$$R_1O[CH_2CH(CH_3)O]_x(CH_2CH_2O)_y[CH_2CH(OH)R_2]$$

wherein $R_1$ is a linear, aliphatic hydrocarbon radical having from about 4 to about 18 carbon atoms including mixtures thereof; and $R_2$ is a linear, aliphatic hydrocarbon radical having from about 2 to about 26 carbon atoms including mixtures thereof; x is an integer having a value from 1 to about 3; y is an integer having a value from 5 to about 30. Also disclosed is an automatic dishwasher composition comprising the above-described epoxy-capped poly(oxyalkylated) alcohol and at least one component selected from the group consisting of detergent builder, bleach, anti-wear agent, and mixtures thereof. Also disclosed is a cleaning composition for cleaning hard surfaces comprising an aqueous or organic solvent and the above-described epoxy-capped poly(oxyalkylated) alcohol as a surfactant.

7 Claims, 1 Drawing Sheet

RINSE EFFICACY

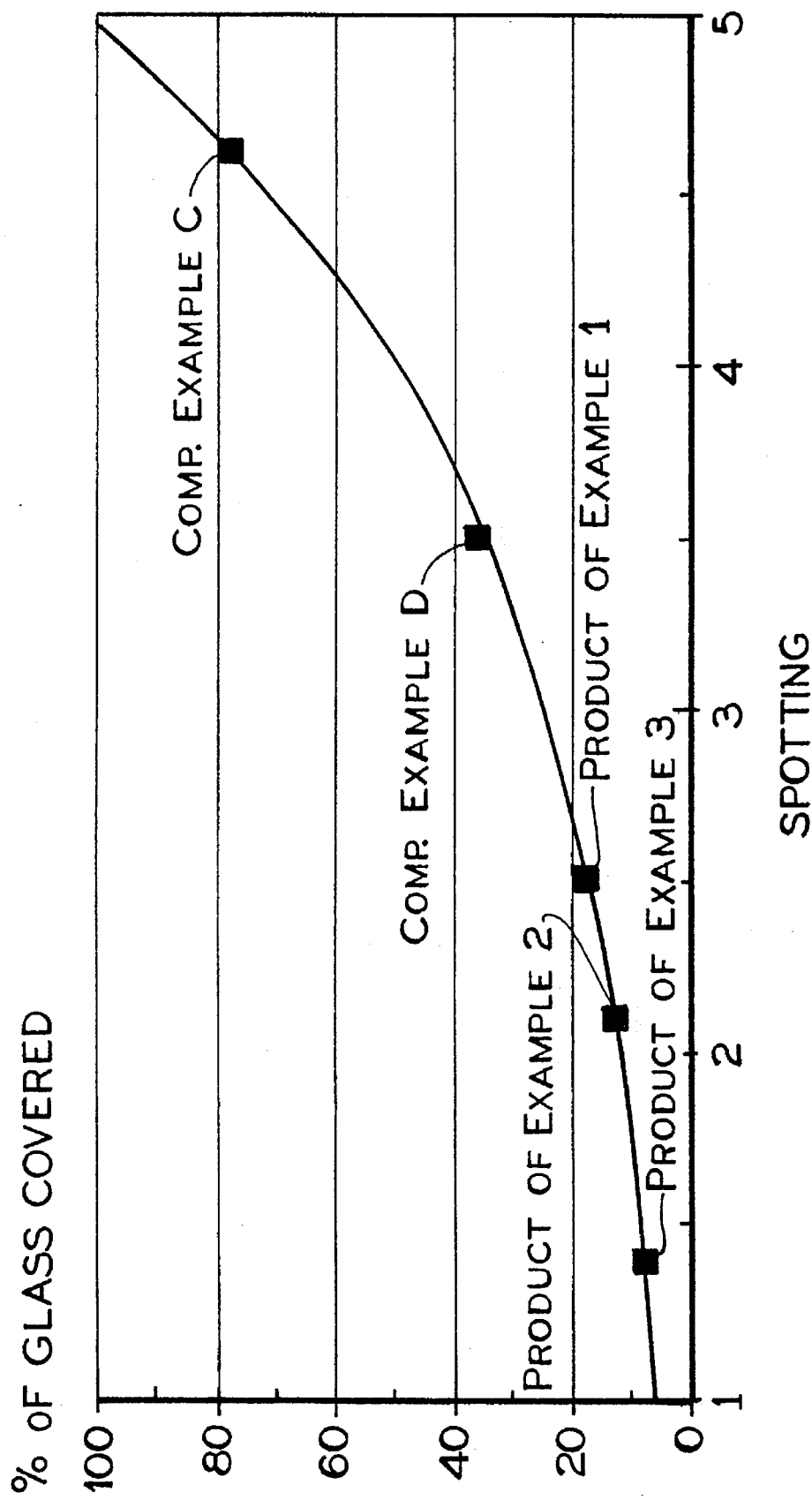

BIOGRADABLE LOW FOAMING SURFACTANTS AS A RINSE AID FOR AUTODISH APPLICATIONS

FIELD OF THE INVENTION

The present invention relates to novel low foaming surface active agents. More particularly, the invention relates to novel low foaming surface active agents having enhanced biodegradability as well as improved performance as rinse aids in automatic dish washing and hard surface cleaner applications.

BACKGROUND OF THE INVENTION

Many of the cleaning compositions heretofore recommended for use in connection with the cleaning of tableware have been subject to one or more significant disadvantages. Perhaps the paramount difficulty involved relates to the tendency of such compositions to leave undesirable spots and films on the washed tableware. As will be recognized, aesthetic considerations rather than purely functional criteria are often of overriding importance in regard to the suitability of a given cleaning composition, especially when contemplated for use in connection with the cleaning of tableware.

Further, environmental concerns have placed a premium on developing surfactants having increased biodegradability. Biodegradability is defined as that property possessed by a material enabling it to be decomposed by bacteria or other living organisms.

Ideally, surfactants utilized in the washing of tableware in automatic dishwashers will have a combination of biodegradablity characteristics and improved rinsing properties.

The prior art is replete with the disclosure of various surfactant compositions. By way of illustration, U.S. Pat. No. 3,956,401 discloses liquid surfactants having the formula:

$$RO-(CH_2-CH-O)_x-(CH_2-CH_2-O)_y-(CH_2-CH-O)_z-H$$
$$\phantom{RO-(CH_2-}|\phantom{CH-O)_x-(CH_2-CH_2-O)_y-(CH_2-}|$$
$$\phantom{RO-(CH_2-}R'\phantom{CH-O)_x-(CH_2-CH_2-O)_y-(CH_2-}R''$$

wherein R is a substantially linear hydrocarbon and more particularly an alkyl group having an average of from about 7 to about 10 carbon atoms; R' is a linear, alkyl hydrocarbon of from about 1 to about 4 carbon atoms; R" is a linear, alkyl hydrocarbon of from about 1 to about 4 carbon atoms; x is an integer of about 1 to about 6; y is an integer of about 4 to about 15; and z is an integer of about 4 to about 25.

As another illustration, U.S. Pat. No. 4,925,587 discloses hydroxyalkyl polyethylene glycol and hydroxyalkyl polypropylene glycol ether surfactants corresponding to the following general formula:

$$\phantom{R^1-CH-}OH\phantom{-CH_2-(OCH-}R^3$$
$$\phantom{R^1-CH-}|\phantom{-CH_2-(OCH-}|$$
$$R^1-CH-CH_2-(OCH-CH_2)_n-OR^2$$

in which $R^1$ is a linear $C_6$–$C_{16}$ alkyl radical;

$R^2$ is a linear or branched, saturated or unsaturated $C_1$–$C_{22}$ alkyl radical;

$R_3$ is hydrogen or a methyl group; and n is a number of from 0 to 30.

As yet another example, U.S. Pat. No. 4,317,940 discloses biodegradable surfactants described as being useful as agricultural emulsifiers and having the following general formula:

$$RO-(CH_2-CH-O)_x-(CH_2-CH_2-O)_y-(CH_2-CH-O)_z-H$$
$$\phantom{RO-(CH_2-}|\phantom{CH-O)_x-(CH_2-CH_2-O)_y-(CH_2-}|$$
$$\phantom{RO-(CH_2-}R'\phantom{CH-O)_x-(CH_2-CH_2-O)_y-(CH_2-}R''$$

wherein R is a linear, alkyl hydrocarbon chain having an average of from about 6 to about 10 carbon atoms; R' is a linear, alkyl hydrocarbon of 1 to about 4 carbon atoms; R" is a linear, alkyl hydrocarbon of from about 1 to about 4 carbon atoms; x is an integer of from about 8 to about 12; y is an integer from about 19 to about 25; and z is an integer from about 2 to 7.

As still yet another illustration, U.S. Pat. No. 4,827,028 discloses the production of anionic surfactants by reacting an unsaturated dicarboxylic acid such as maleic acid or fumaric acid with at least one epoxy-capped poly(oxyalkylated) alcohol having the formula (A) and (B):

$$R-O-(CH_2-CH-O)_x-(CH_2-CH_2-O)_y-CH_2-CH-R_1 \quad (A)$$
$$\phantom{R-O-(CH_2-}|\phantom{CH-O)_x-(CH_2-CH_2-O)_y-CH_2-}|$$
$$\phantom{R-O-(CH_2-}CH_3\phantom{CH-O)_x-(CH_2-CH_2-O)_y-CH_2-}OH$$

$$R-O-(CH_2-CH_2-O)_y-(CH_2-CH-O)_x-CH_2-CH-R_1 \quad (B)$$
$$\phantom{R-O-(CH_2-CH_2-O)_y-(CH_2-}|\phantom{CH-O)_x-CH_2-}|$$
$$\phantom{R-O-(CH_2-CH_2-O)_y-(CH_2-}CH_3\phantom{CH-O)_x-CH_2-}OH$$

wherein R is a hydrocarbon containing radical having from 1 to about 8 carbon atoms; $R_1$ is a hydrocarbon containing radical having from about 6 to about 18 carbon atoms; x is an integer having a value from about 6 to about 40 and y is an integer having a value from about 8 to about 50. The ratio of x:y is from about 2:8 to about 8:2; and the mole ratio of dicarboxylic acid to epoxy-capped poly(oxylalkylated) alcohol is from about 1:1 to about 10:1.

The above-described surfactants typically have high caustic solubility, which can be an important surfactant characteristic. Unfortunately, an increased emphasis on biodegradability and surfactant cleaning performance in the cleaning of tableware, particularly when utilizing detergent compositions having low phosphate concentrations, has resulted in requirements which are not completely satisfied utilizing the compositions described in the above-referenced patents.

BRIEF SUMMARY OF THE INVENTION

New nonionic surfactants have been discovered which have surprisingly improved rinsing characteristics, are readily biodegradable, and are low foaming. Their use results in a significant reduction in spotting and filming of tableware, as compared to conventional surfactants, when used in automatic dishwashers.

The novel compositions are epoxy-capped poly(oxyalkylated) alcohols represented by the formula:

$$R_1O[CH_2CH(CH_3)O]_x(CH_2CH_2O)_y[CH_2CH(OH)R_2]$$

wherein $R_1$ is a linear, aliphatic hydrocarbon radical having from 4 to 18 carbon atoms including mixtures thereof; and $R_2$ is a linear, aliphatic hydrocarbon radical having from 2 to 26 carbon atoms including mixtures thereof; x is an integer having a value from 1 to 3; y is an integer having a value from 5 to 30. Preferred surfactant compositions include those in which x is an integer having a value from about 1 to about 2, and more preferably 1. Also preferred are surfactant compositions in which y is an integer having a value from about 10 to about 25, and more preferably from about 10 to about 20 With respect to z, preferred embodiments are those in which z has a value of from 1 to about 2, and most preferably 1.

In another aspect, the present invention relates to an automatic dishwasher composition comprising the above-described epoxy-capped poly(oxyalkylated) alcohol and at least one component selected from the group consisting of detergent builder, bleach, anti-wear agent, and mixtures thereof.

In yet another aspect, the present invention relates to a cleaning composition for cleaning hard surfaces comprising an aqueous or organic solvent and the above-described epoxy-capped poly(oxyalkylated) alcohol as a surfactant.

These and other aspects will become apparent upon reading the following detailed description of the invention.

BRIEF DESCRIPTION OF THE DRAWINGS

The FIGURE is a graph showing the rinse efficacy of the products of the invention, EXAMPLES 1, 2 and 3, and COMPARATIVE EXAMPLES C and D with respect to spotting of washed glassware.

DETAILED DESCRIPTION OF THE INVENTION

Basically, the surfactant compositions of the present invention consist of four components, namely a linear alcohol, propylene oxide, ethylene oxide, and an epoxy cap. The epoxy cap and the linear alcohol serve as a hydrophobic, oil-soluble portion of the molecule. The ethylene oxide groups form the hydrophilic, water-soluble elements of the molecule.

It has been surprisingly discovered in accordance with the present invention that significant improvements in biodegradability and rinsing characteristics, relative to conventional surfactants, are provided utilizing the compositions of the present invention to clean tableware. Without wishing to be bound by any particular theory, the present inventors believe that this improvement is at least partly attributable to the ordered structure of the compositions in which limited numbers of propylene oxide groups are directly attached to the alcohol followed by addition of the ethylene oxide groups and capping using the 1,2-epoxyalkane. While maintaining this ordered structure, it is desired to also have low ratios of propylene oxide groups to ethylene oxide groups. For example, preferred ratios of propylene oxide groups to ethylene oxide groups are in the range of about 1:5 to about 1:30, and more preferably from about 1:10 to about 1:20.

Generally, these poly(oxyalkylated) alcohols may be made by condensing an aliphatic alcohol, or mixture of alcohols, having an average chain length of from 4 to about 18 carbon atoms, preferably from about 4 to about 12, and more preferably from about 6 to about 10 carbon atoms, initially with propylene oxide followed by capping this condensation product with ethylene oxide. The methods used for condensing and capping may be any of the well-known methods described in the art. Preferably, these reactions occur at elevated temperatures in the range of about 120° C. to about 180° C., and more preferably at from about 140° C.–160° C. It is also preferred to carry out such reactions in the presence of an effective amount (e.g. about 0.005% to 1% by weight of the alcohol) of a suitable alkaline catalyst(s) such as hydroxides of alkali metals or alkaline earth metals as well as alkali metal alcoholates and $BF_3$. The preferred catalyst is KOH.

Epoxy compounds useful for making the epoxy-capped poly(oxyalkylated) alcohols of the present invention include any 1,2-epoxyalkanes, or mixtures thereof, having a hydrocarbon chain containing an average of about 2 to about 26 carbon atoms. Preferably, the 1,2-epoxyalkane has a linear, aliphatic hydrocarbon chain containing an average of from about 8 to about 20 carbon atoms, and more preferably an average of from about 10 to about 16 carbon atoms. Generally, 2 to 4 carbons is preferred if a high cloud point composition is desired, 6 to 10 carbons is preferred to optimize defoaming efficacy, and 12 to 22 carbons is desired to optimize rinsing efficacy. Various 1,2-epoxyalkane compounds are commercially available from Atochem North America Inc., Philadelphia, Pa. under the product names VIKALOX 11-14, VIKALOX 12, VIKALOX 16 and others.

The novel surfactant compositions of the present invention provide improved surface treatment of the tableware by the rinse water and subsequently reduces spotting and filming. These epoxy-capped poly(oxyalkylated) alcohols can be formulated in powder and liquid detergent products for automatic dishwashers or in hard surface cleaning products, such as bathroom tile, using methods commercially practised in the detergent industry. These formulations can include, for example, detergent builders, chelating agents, bleaches, anti-wear agents, and combinations thereof, among others.

Suitable detergent builders include inorganic builders such as sodium tripolyphosphate (STPP), sodium carbonate, zeolites and mixtures thereof. Where STPP is the detergent builder, the STPP may be employed in the compositions in a range of about 8 to 35 wt. %, preferably about 20 to 30 wt %, and should preferably be free of heavy metal which tends to decompose or inactivate the preferred sodium hypochlorite and other chlorine bleach compounds. The STPP may be anhydrous or hydrated, including the stable hexahydrate with a degree of hydration of 6 corresponding to about 18% by weight of water or more.

Organic builders can also be used including nitrilotriacetic acid and alkali metal salts of tartaric or citric acid.

Where used, a chelating agent can be any one of a wide range of organic or inorganic sequestering agents, examples including phosphoric acid, amino polycarboxylic acids such as EDTA, NTA and DETPA, and polycarboxylic acids such as lactic acid, citric acid, tartaric acid, gluconic acid, glucoheptonic acid, mucic acid, galactonic acid, saccharic acid, fumaric acid, succinic acid, glutaric acid, adipic acid and their alkali metal or ammonium salts. Citric or tartaric acid are preferred chelating acids. The chelating agent if included is present in an amount of up to about 30% and normally lies in the range from about 5% to about 20% by weight. Highly preferred compositions use from about 5% to about 10% by weight of chelating agent in order to minimize any attack by the chelating agent on the glass.

When a bleach is a component in the formulation, the bleach may be an organic chlorine containing bleach, for example, trichloroisocyanuric acid, dichloroisocyanuric acid or a salt of dichloroisocyanuric acid. Preferably a sodium or potassium salt such as trichloroisocyanuric acid and is employed in an amount of, for example, 1 to 5% and more preferably 2 to 3% by weight in the cleaning composition. Inorganic bleaching compounds such as chlorinated trisodium polyphosphate (TSPP) or lithium hypochlorite may also be used.

The dishwasher formulations may also include anti-wear or anti-corrosion agents such as an alkali metal silicate, preferably sodium silicate, and may be present in a ratio of 0.1 to 3 and preferably 0.2 to 1 mole per mole of alkali in the cleaning composition.

Alkalinity may be provided by an alkali metal compound, for example, sodium or potassium hydroxide and/or carbonate.

Further suitable conventional ingredients for inclusion in the compositions are hydrotropic agents such as xylene sulfonates, alcohols, perfumes and coloring agents.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

The following examples are provided to further illustrate the invention. All parts and percentages are by weight unless otherwise specified.

EXAMPLE 1

To a 1000 ml round bottom 3-necked flask fitted with a thermometer, on which is placed a thermowatch sensor, a magnetic stirring bar, an equilibrated dropping funnel fitted with a nitrogen inlet, a dry-ice/acetone condenser, and a nitrogen outlet, was added 100 grams (0.6827 moles) of Alfol-610 (Vista Chemical) and 0.4 grams (0.007 moles) of KOH. The alcohol is stirred and heated to 140° C. for 1.5 hours. At the end of this time 39.60 grams (0.6827 moles) of propylene oxide was added dropwise over one hour. The reaction was complete when refluxing ceased in the dry-ice/acetone condenser. The mixture was post reacted for 1.5 hours at 140° C. Ethylene oxide, 450.58 grams (10.24 moles) was then added slowly over 6–8 hours under slow reflux. The reaction mixture was then post-reacted for 1.5 hours at 140° C. At the end of this time 151.1 grams (0.629 moles) of 1,2-epoxyhexadecane (Atochem) was added through the dropping funnel. The addition took place over a period of less than 10 minutes. The reaction mixture was post-reacted at 160°±3° C. for 4.5 hours. At the end of this time the solid product was cooled and removed from the flask. The cloud point of a one percent solution of the product in water was <1° C. The hydroxyl number was 56.2 and the primary hydroxyl content was 18.3%.

EXAMPLE 2

To the identical apparatus used in Example 1 was added 100 grams (0.6827 moles) of Alfol-610 (Vista Chemical) and 0.4 grams (0.007 moles) of KOH. The alcohol was stirred and heated to 140° C. for 1.5 hours. At the end of this time 39.60 grams (0.6827 moles) of propylene oxide was added dropwise over one hour. When refluxing ceased in the dry-ice/acetone condenser the reaction was complete. The mixture was post reacted for 1.5 hours at 140°° C. Ethylene oxide, 600.78 grams (13.654 moles) was then added slowly over 6–8 hours under slow reflux. The reaction mixture was then post-reacted for 1.5 hours at 140° C. To the reaction mixture 116.2 grams (0.480 moles) of 1,2-epoxyhexadecane (Atochem) was added through the dropping funnel in less than 10 minutes. The reaction mixture was post-reacted at 160°±3° C. for 4.5 hours. At the end of this time the solid product was cooled and removed from the flask. The cloud point of a one percent solution of the product in water was 8° C. The hydroxyl number was 48.7 and the % primary hydroxyl was 19.7.

EXAMPLE 3

Using the identical apparatus of Examples 1 and 2, 100 grams (0.6827 moles) of Alfol-610 (Vista Chemical) and 0.4 grams (0.007 moles) of KOH were added to the flask. The alcohol was stirred and heated to 140° C. for 1.5 hours. At the end of this time 39.60 grams (0.6827 moles) of propylene oxide was added dropwise over one hour. The reaction was completed when refluxing ceased in the dry-ice/acetone condenser. The mixture was post reacted for 1.5 hours at 140° C. Ethylene oxide, 600.78 grams (13.654 moles) was then added slowly over 6–8 hours under slow reflux. The reaction mixture was then post-reacted for 1.5 hours at 140° C. Next 74.88 grams (0.480 moles) of 1,2-epoxydecane (Atochem) was added through the dropping funnel in a period of less than 10 minutes. The reaction mixture was post-reacted at 160°±3° C. for 4.5 hours. At the end of this time the solid product was cooled and removed from the flask. The cloud point of a one percent solution of the product in water was 14° C. The hydroxyl number was 53.0 and the primary hydroxyl content was 25.6%.

EXAMPLES 4–6 AND COMPARATIVE EXAMPLES A, B AND C

Loads of tableware including ten 9 inch dinner plates, 10 soda glasses, and assorted tableware were subjected to 5 washing cycles in a Hobart Superba model dishwasher. The washing cycles comprised one wash cycle and two rinses. The maximum temperature during the wash cycle is approximately 137° F. and the tableware washing is completed in 70 minutes.

The tableware were washed with each of the products of Examples 1, 2 and 3. In addition, the tableware was washed under identical conditions with a commercial surfactant, Cascade (Procter & Gamble Co.). As additional comparisons, the formulation of Comparison B was tested under identical conditions utilizing the surfactant of Example 8 of U.S. Pat. No. 3,956,401, and Comparison C utilized the surfactant of Example 7b of U.S. Pat. No. 4,925,587. For each washing cycle 20 grams of detergent, including 0.6 grams of surfactant, were used. After each washing, the glassware was evaluated for spotting, streaking and filming using a scale of 1 to 5 in which 1 shows no spots, streaks or film, and 5 indicates the glasses were completely covered with spots, streaks and film. This testing procedure closely follows the Chemical Specialties Manufacturing Association (CSMA) Test procedure DCC 05A. The results are given in Table I below.

TABLE I

| | Glassware Rinsing In Automatic Dishwasher | | |
|---|---|---|---|
| Example No. | Spotting | Streaking | Filming |
| 4. Product of Example 1 | 2.5 | 1.0 | 1.7 |
| 5. Product of Example 2 | 2.1 | 1.0 | 2.1 |
| 6. Product of Example 3 | 1.4 | 1.0 | 3.1 |
| Comp. A, Cascade | 3.5 | 1.0 | 3.3 |
| Comp. B, Example of U.S. Pat. No. 3,956,401 | 3.5 | 1.0 | 3.4 |
| Comp. C, Example 7b of U.S. Pat. No. 4,925,587 | 4.7 | 1.0 | 3.9 |

Glassware cleaned using the products of the invention clearly show a significant improvement in spotting and filming over the commercial detergents. The spotting data is shown graphically in FIG. 1.

EXAMPLE 7 AND COMPARATIVE EXAMPLES D AND E

An Automatic Dishwashing Foam Test (CSMA DCC-01) was used to evaluate products of this invention. Also tested were a commercial product, Cascade (Procter & Gamble) and the product of Example 7b of U.S. Pat. No. 4,925,587.

Milk and egg soils were employed in these tests. Measurements were made of the ratio of the revolutions of the dishwasher rotor with detergent and soil as a percentage of the revolutions with water alone. The higher the ratio, the more efficient is the detergent. From the results provided in Table 2 hereinbelow, it is readily apparent that the product of this invention compares very favorably with the comparative example products. Results are shown in Table 2.

TABLE 2

Defoaming Studies in Automatic Dishwasher

| Example # | Milk Soil % | Egg Soil % |
|---|---|---|
| 7. Product of Example 3 | 99 | 98 |
| Comp D., Cascade | 91 | 94 |
| Comp E., Example 7b of U.S. Pat. No. 4,925,587 | 100 | 67 |

What is claimed is:

1. An automatic dishwasher composition comprising an epoxy-capped poly(oxyalkylated) alcohol represented by the formula:

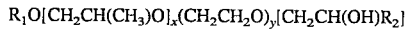

$$R_1O[CH_2CH(CH_3)O]_x(CH_2CH_2O)_y[CH_2CH(OH)R_2]$$

wherein $R_1$ is a linear, aliphatic hydrocarbon radical having from 4 to 18 carbon atoms including mixtures thereof; and $R_2$ is a linear, aliphatic hydrocarbon radical having from 2 to 26 carbon atoms including mixtures thereof; x is an integer having a value from 1 to 3; y is an integer having a value from 5 to 30, the ratio of x:y being between about 1:5 and about 1:30, and at least one component selected from the group consisting of detergent builder, bleach, anti-wear agent, and mixtures thereof.

2. The automatic dishwasher composition of claim 1 wherein said $R_2$ in said formula has an average of from about 2 to about 14 carbon atoms.

3. The automatic dishwasher composition of claim 1 wherein said x in said formula is from 1 to about 2.

4. The automatic dishwasher composition of claim 1 wherein said y in said formula is from about 10 to about 25.

5. The automatic dishwasher composition of claim 1 wherein said $R_1$ in said formula has an average of from about 4 to about 12 carbon atoms.

6. The automatic dishwasher composition of claim 1 wherein said x in said formula is 1.

7. The automatic dishwasher composition of claim 1 wherein said y in said formula is from about 10 to about 20.

* * * * *